United States Patent [19]

Bergthaller et al.

[11] 4,446,219
[45] May 1, 1984

[54] PHOTOGRAPHIC MATERIAL COMPRISING A LAYER WITH NI COMPLEX OF 2,2'-BISPHENOL

[75] Inventors: Peter Bergthaller; Jürgen Strauss, both of Cologne, Fed. Rep. of Germany

[73] Assignee: Agfa-Gevaert Aktiengesellschaft, Leverkusen, Fed. Rep. of Germany

[21] Appl. No.: 406,307

[22] Filed: Aug. 9, 1982

[30] Foreign Application Priority Data

Aug. 17, 1981 [DE] Fed. Rep. of Germany ..... 31323332

[51] Int. Cl.³ .................. G03C 1/40; G03C 5/54; G03C 7/00
[52] U.S. Cl. .................................... 430/216; 430/213; 430/222; 430/223; 430/372
[58] Field of Search ............... 430/213, 216, 223, 372, 430/551, 222; 524/171, 155, 325, 328

[56] References Cited

U.S. PATENT DOCUMENTS

| | | | |
|---|---|---|---|
| 3,072,601 | 1/1963 | Breslow | 524/328 |
| 3,282,887 | 11/1966 | Soeder | 524/171 |
| 3,700,455 | 10/1972 | Ishikawa et al. | 430/551 |
| 3,843,597 | 10/1974 | Stretanski et al. | 524/328 |
| 4,013,620 | 3/1977 | Henderson et al. | 524/328 |
| 4,050,938 | 9/1977 | Smith et al. | 430/554 |
| 4,273,854 | 6/1981 | Hara et al. | 430/216 |

Primary Examiner—Richard L. Schilling
Attorney, Agent, or Firm—Connolly & Hutz

[57] ABSTRACT

In a photographic material suitable for use as image receptor element for the dye diffusion transfer process, a dyeable layer arranged on a layer support contains nickel chelates of a 2,2'-bisphenol corresponding to one of the general formulae I and II as metallizing agents for the formation of colored complexes of organic colorless or colored complex formers. The chelatizable image dyes which are transferred image-wise into the dye absorbent layer in the process of development give rise to the corresponding nickel complexes which have improved light stability.

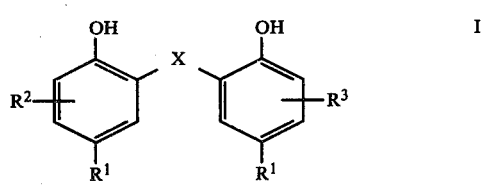

I

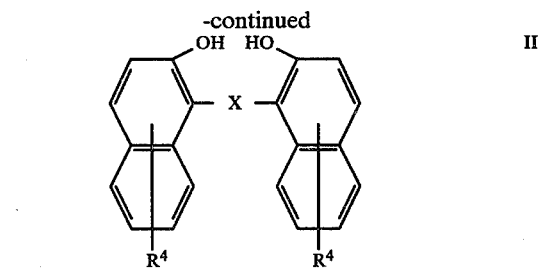

II $X = S$,

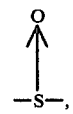

or $-SO_2-$;

$R^1$ = a hydrocarbon group optionally attached through $-O-$ or a halogen or $R^4$;
$R^2$ = hydrogen, halogen, alkyl or alkoxy, alkenyl a condensed benzene ring or $R^4$ if $R^1$ does not denote a group $R^4$;
$R^3 = R^2$ or

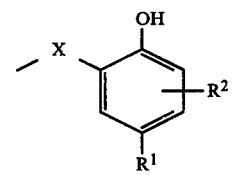

$R^4 = -CO-O-R^5$,

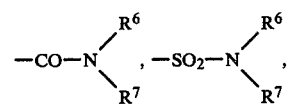

$-NH-CO-R^2$ or $-NH-SO_2-R^9$;
$R^5$ = alkyl, aralkyl or cycloalkyl;
$R^6$, $R^7$ = hydrogen, alkyl, aralkyl, aryl, cycloalkyl or together denote a residue for completing a cyclic amino group;
$R^8$ = alkyl, aralkyl, aryl,

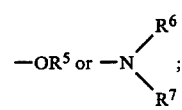

and
$R^9$ = alkyl, aryl or

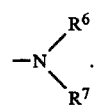

5 Claims, No Drawings

PHOTOGRAPHIC MATERIAL COMPRISING A LAYER WITH NI COMPLEX OF 2,2'-BISPHENOL

This invention relates to a photographic material in which a layer arranged on a layer support and capable of being colored by organic dyes contains a metallizing agent for the formation of organic dye-metal complexes. The invention relates in particular to an image receptor element for the production of color photographic images by the dye diffusion transfer process in which diffusible dyes which can be metallized subsequently are used for producing the color image. The metallizing agents used according to the invention are nickel complexes of 2,2'-thio-bisphenols, 2,2'-sulfinyl-bisphenols or 2,2'-sulfonyl-bisphenols contained in the dye absorbent layer.

The use of polyvalent metal cations, in particular complex forming metal cations, is of particular interest for use in image receptor layers for the photographic dye diffusion transfer process. As is known, the dye diffusion transfer process, which is particularly important for instant color photography, is carried out using a light-sensitive recording material comprising several silver halide emulsion layers of differing spectral sensitivities and color providing compounds associated with these layers. The color providing compounds used may be, for example, so called dye developers, which are originally diffusible compounds having a chromophoric residue and a developer function which immobilizes the compounds image-wise during development, or non-diffusing color-providing compounds having a chromophoric residue which is released image-wise in the course of development as a diffusible dye or dye precursor (dye-releaser). If the chromophoric residue of the dye developer or of the dye-releasers contains special substituents suitable for use as ligands for complex formation with polyvalent metal cations, it is possible to utilize the complex formation for improving the stability to light, influencing the color tone and fixing the image dyes which have been transferred into the image receptor layer. Complex formation is preferably carried out only after dye transfer has taken place and may be achieved either by treating the image receptor material with a solution of the complex-forming polyvalent metal cations, e.g. in the form of a solution of the corresponding salts, or by incorporating the polyvalent metal cations in one or more layers of the image receptor material so that they are capable of immediately reacting with the dyes diffusing into their layers in the course of development to form complexes with them.

Polymers containing polyvalent metal cations bound in complex form and their use in image receptor layers of color photographic materials for the dye diffusion transfer process have been described in Research Disclosure No. 18534 (September 1979). The polymers described there, however, have only a limited capacity for taking up polyvalent metal cations.

EP-A No. 0,009,411 discloses that the cationic nickel or copper complexes of polyvinyl pyridine or polyvinyl imidazole may be used as metallizing agents for image dyes which are capable of subsequent complex formation. Although these complexes have little color of their own at a neutral pH, they rapidly assume a reddish-yellow color at the pH of an alkaline processing medium. They lose this color only very slowly, generally over a period of days, and during this time the color renders the picture unsightly. Moreover, the proportion of co-ordinate hetero-aromatically bound nitrogen atoms which remains bound to the dye-metal complex adversely affects the shade of the picture tone, particularly in the case of cyan dye complexes. In most cases, an undesirable short shift of the absorption band occurs which shifts the color tone towards blue.

It is also known from the aforesaid European Patent application that metal complexes of polymers with imino diacetic acid units may be used as metallizing agents. These metallizing agents are difficult to handle by the methods of polymer chemistry and are liable to agglomerate, especially in the case of latex polymers.

SUMMARY OF THE INVENTION

It is an object of the present invention to provide a metallizing agent which can be introduced particularly easily by the diffusion process into a dye absorbent layer of a photographic material, in particular an image receptor element for color photographic images, which contains metal ions, specifically nickel ions, bound in a diffusion-fast form, and which does not agglomerate with cationic mordants and has no disadvantages for the image produced, in particular no self color.

It has been found that metallizing agents satisfying the requirement indicated above may be prepared particularly simply by reacting 2,2'-thio-bis-phenols, 2,2'-sulfinyl-bis-phenols or 2,2'-sulfonyl-bis-phenols with nickel salts, optionally in the presence of auxiliary bases. The water-insoluble nickel complex compounds formed may be added to the casting solutions for the dye absorbent layers in the form of aqueous dispersions, optionally in the presence of high-boiling, water-insoluble oil formers.

The present invention thus provides a photographic material having a layer capable of being colored by organic dyes, which layer is arranged on a layer support and contains a metallizing agent for the formation of organic dye-metal complexes, characterized in that the layer capable of absorbing organic dyes contains, as metallizing agent, a water-insoluble nickel complex formed from a 2,2'-bis-phenol corresponding to one of the following general formulae I and II:

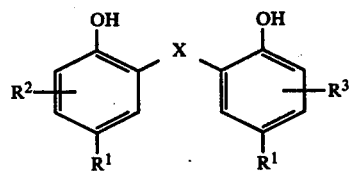

I

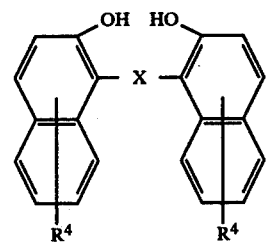

II wherein
X denotes —S—,

or —SO$_2$—;

R$^1$ denotes a hydrocarbon residue having up to 18 C-atoms, which residue is attached either directly or through —O—; or it denotes halogen, in particular chlorine, or a group R$^4$;

R$^2$ denotes hydrogen, halogen, in particular chlorine, alkyl or alkoxy with up to 18 C-atoms, alkenyl, e.g. allyl or methallyl, a residue for completing a condensed benzene ring; or a group R$^4$, provided R$^1$ does not denote a group R$^4$;

R$^3$ denotes a residue as defined for R$^2$ or a group corresponding to the formula:

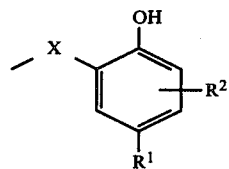

wherein
X, R$^1$ and R$^2$ have the meaning indicated above,
R$^4$ denotes —CO—O—R$^5$,

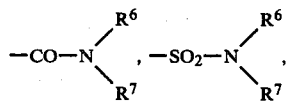

—NH—CO—R$^8$ or —NH—SO$_2$R$^9$,

R$^5$ denotes alkyl, aralkyl, or a cycloalkyl with up to 8 C-atoms:

R$^6$ and R$^7$ denote hydrogen, alkyl, aralkyl, aryl or cycloalkyl or together they denote a residue for completing a 5-, 6- or 7-membered cyclic amino group (pyrrolidine, piperidine, perhydroazepine or morpholine);

R$^8$ denotes alkyl, aralkyl, aryl,

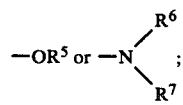

and
R$^9$ denotes alkyl, aryl or

DETAILED DESCRIPTION OF THE INVENTION

The residues R$^1$, R$^2$, R$^3$ and R$^4$ shown in formulae I and II function in particular as ballast groups, i.e. the size of all the residues R$^1$, R$^2$ and R$^3$ (I) or R$^4$ (II) as a whole is such that the nickel complexes formed from the compounds will be incorporated in a diffusion-fast form in photographic layers.

The hydrocarbon groups denoted by R$^1$ may be, for example, alkyl, aralkyl, cycloalkyl or aryl groups. Specific examples include n-butyl, tertiary butyl, tertiary amyl, tertiary octyl, n-dodecyl, 1-phenylethyl, 1-phenylisopropyl and cyclohexyl.

When R$^2$ is a residue for completing a condensed benzene ring, R$^1$ is preferably a group R$^4$. R$^2$ is preferably situated adjacent to OH. When R$^3$ and R$^2$ are not identical, R$^2$ is preferably hydrogen.

Typical bisphenols which may be used for the preparation of nickel chelates suitable for use as metal donors in dye absorbent layers are indicated below.

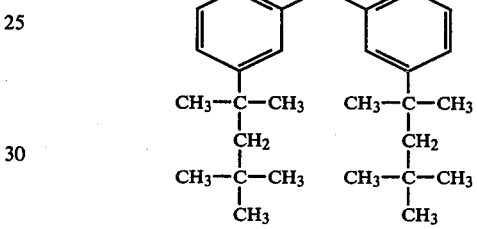

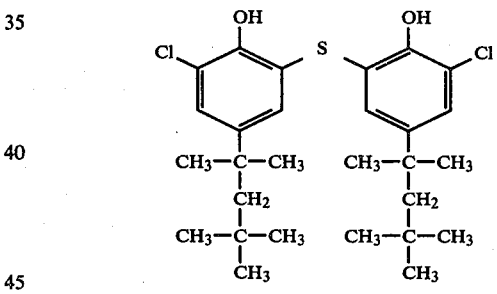

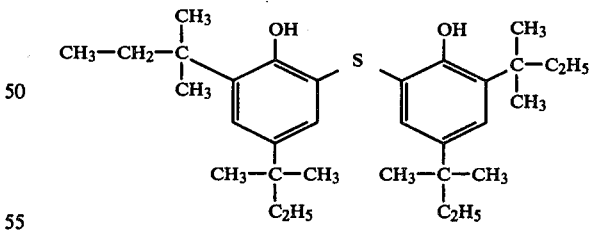

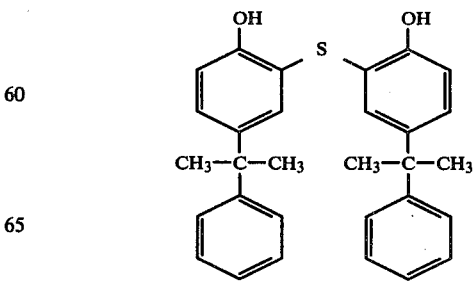

-continued
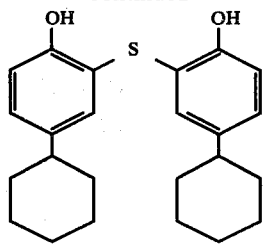
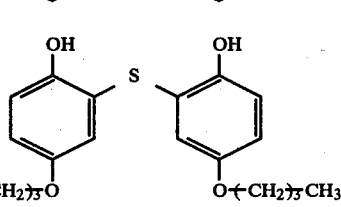
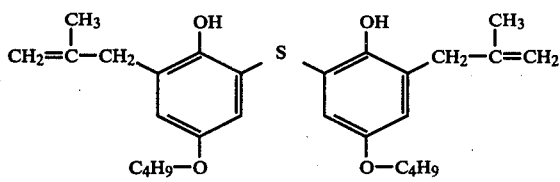
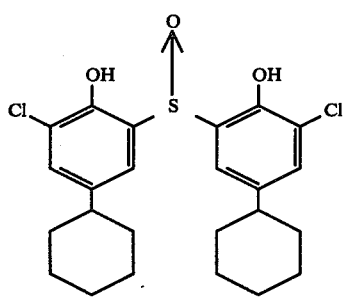
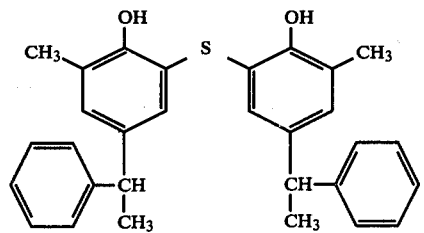
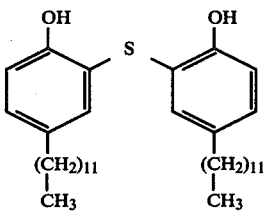
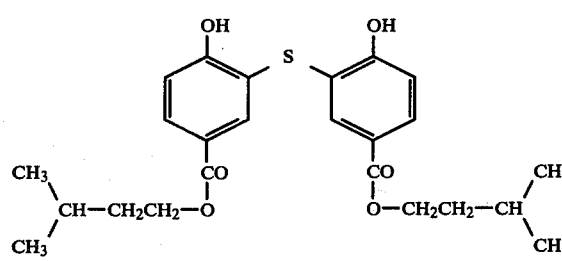
-continued
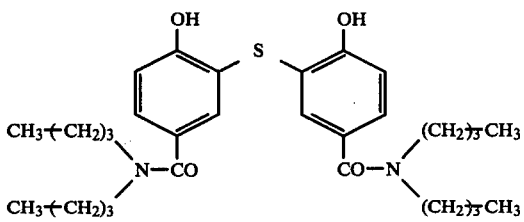
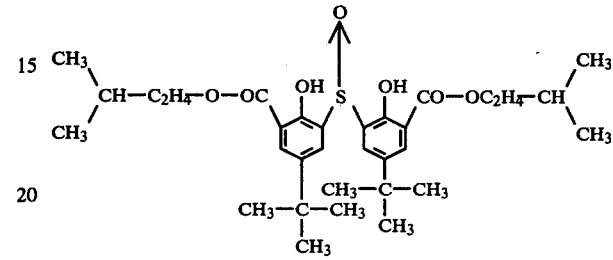
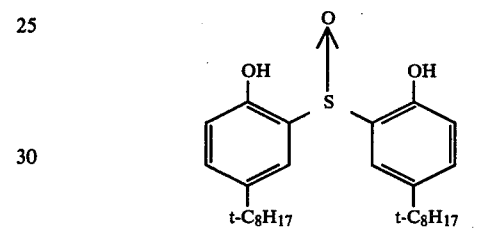
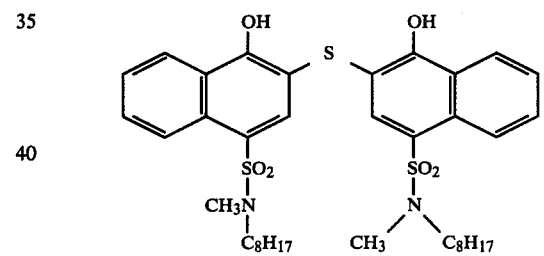
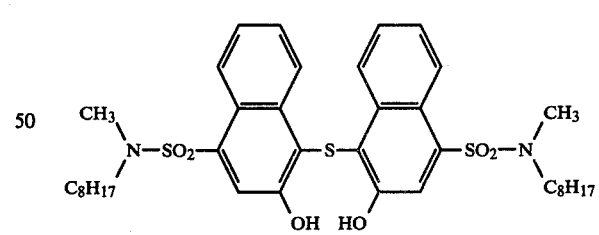
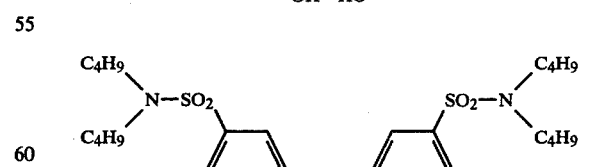
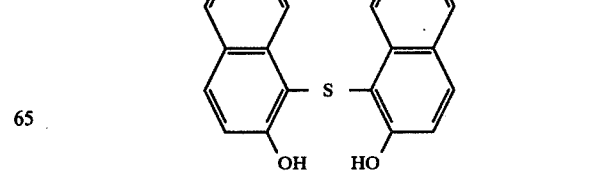

-continued

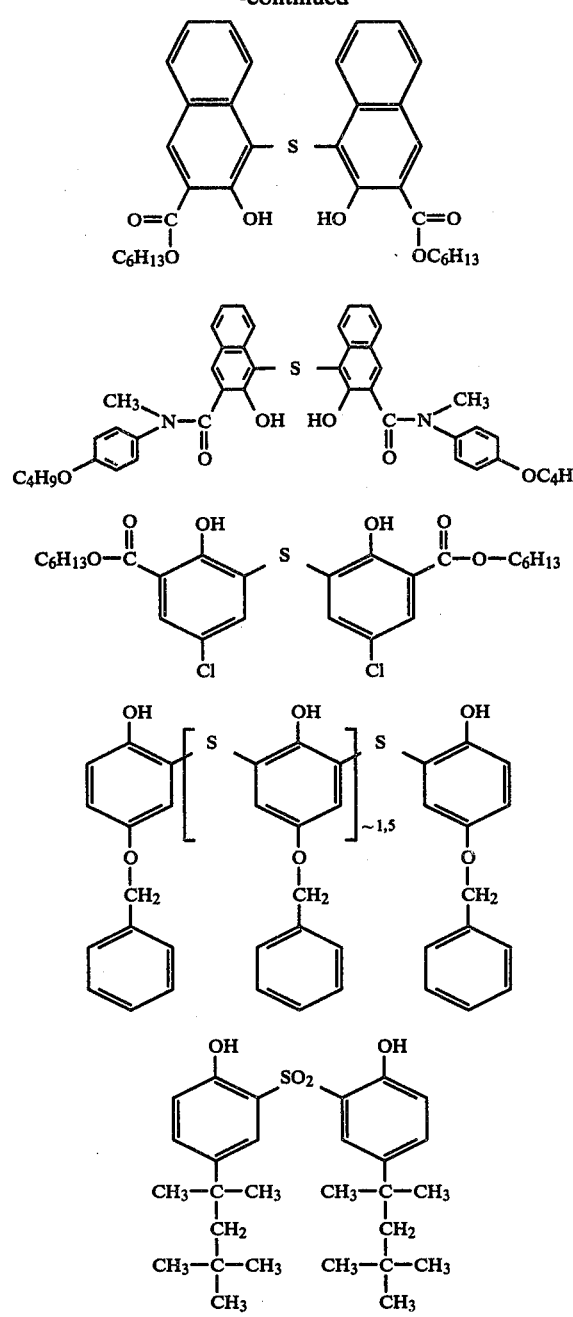

The preparation of 2,2'-thio-bisphenols according to the invention is known in principle and has been described, for example, in British Pat. No. 858,890 and DE-A No. 29 37 294. All the 2,2'-thio-bisphenols mentioned in these documents were prepared by the method described there of reacting the corresponding phenol with the 0.5 molar quantity of sulfur dichloride in the presence of a small quantity of ZnCl₂. If the phenol has two unsubstituted ortho positions to the phenolic hydroxyl group and sulfur dichloride is used in excess, the reaction products contain relatively high molecular weight compounds with 2, 3 or more thio ether bridges and correspondingly 3, 4 or more phenol groups in addition to the thio-bis-phenols (formula I, $R^2=R^3=H$). The sulfoxides and sulfones may be obtained from the thio-bisphenols by mild oxidation with $H_2O_2$ in glacial acetic acid or in dimethyl formamide in the presence of tungstic acid. They are more readily soluble in methanol than the thio bisphenols.

Preparation of Compound 7

Compound 6 was reacted with two equivalents of methallyl chloride in dioxane at room temperature after the addition of two equivalents of sodium hydride and then maintained at 105° C. for 7 hours. The NaCl which separated was removed by suction filtration and the solvent was distilled until a reaction temperature of 150° C. was obtained.

The water-insoluble nickel complexes present in the metallizing agents according to the invention contain 0.5 to 1.5 mol of nickel per mol of bisphenol (I, II). In the case of bisphenols I, they correspond, for example, to the general formula III, IV or V in which the residues or groups have the meaning indicated above and L and L' denote colorless neutral (L) or anionic (L') foreign ligands which were introduced in the course of preparation of the complexes.

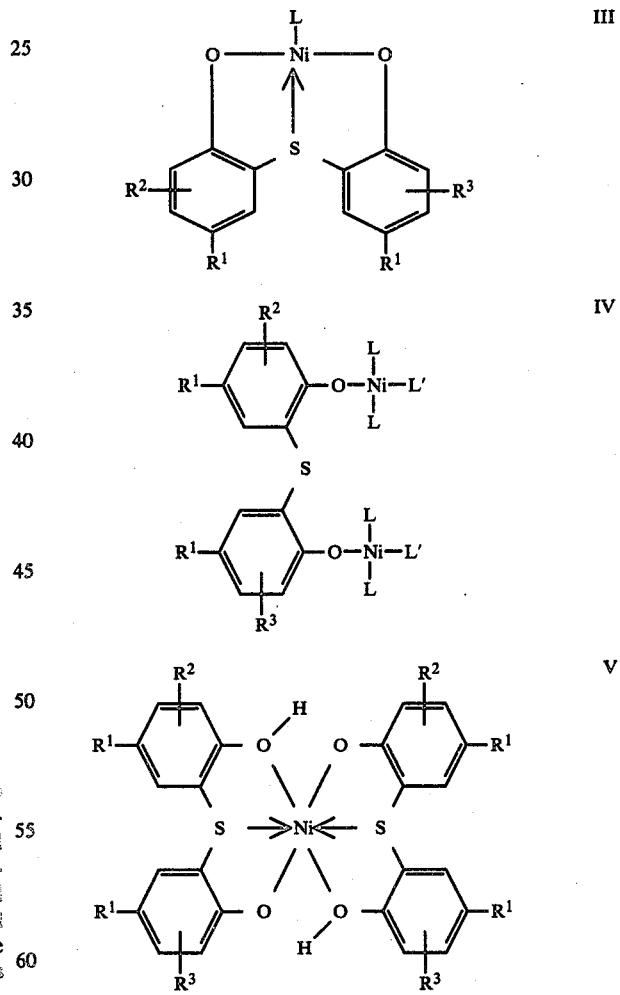

The water-insoluble nickel complexes according to the invention may be prepared by various methods. It is preferred to use those methods in which the bisphenol and optionally an additional ligand are present in a low boiling solvent which is immiscible with water and the nickel salt is introduced as an aqueous or at least partially aqueous phase. The reaction is generally carried out with vigorous stirring and continued until no more nickel is taken up from the aqueous phase. The reaction may be accelerated by heating the mixture or removing part of the solvent by distillation. When the reaction is completed, the aqueous phase, which may contain excess nickel salt, is removed.

The reaction is preferably carried out at pH values above 7, based on the aqueous phase. The base used may be an alkali metal hydroxide, an alkali metal alcoholate, an amine or amidine, an alkali metal phenolate, a water-soluble carbonate or a water-soluble salt of a carboxylic acid.

The following are examples of foreign ligands L which may be carried into the nickel chelate and incorporated with it: a preferably tertiary monoamine or diamine or amidine, e.g. ethyl diisopropylamine, bis-2-hydroxyethylcyclohexylamine, pyridine, diazabicyclo[2,2,2]octane, 1,8-diazabicyclo[5,4,0]-7-undecene, 1,5-diazabicyclo[4,3,0]non-5-ene, a diester or triester of phosphorous acid, e.g. tributyl phosphite, an aliphatic, cycloaliphatic or araliphatic alcohol, a glycol monoether or the corresponding anion.

Some examples of the preparation of nickel chelates according to the invention are given below.

Nickel complex 1

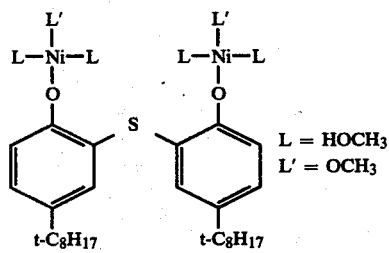

This complex is prepared according to the method given in DE-A No. 1 768 258 by boiling the starting compounds (Compound 1+nickel acetate in a molar ratio of 1:2) in methanol in the presence of the calculated quantity of sodium methylate. The complex is pale green and completely soluble in toluene or ethyl acetate.

Nickel complex 2

11.8 g (26 mmol) of Compound 1 (prepared according to the particulars given in British Pat. No. 858,890, Mp:134°–135° C.), 18.4 ml (108 mmol) of ethyl diisopropylamine, 80 ml of toluene and a solution of 12.4 g (54 mmol) of nickel chloride in 20 ml of water were stirred on a steam bath for 24 hours after the addition of 2.4 g of NaOH in 10 ml of water. The organic phase (toluene) was decanted from the aqueous phase and concentrated by evaporation. Yield 11.1 g (80% of theoretical yield):

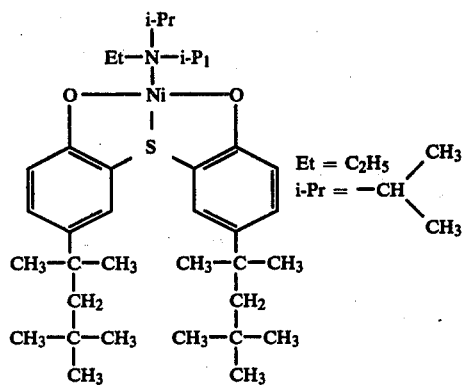

Nickel complex 3

1.5 g of diazabicyclo[2,2,2]octane were introduced into a suspension in 120 ml of toluene of the [2,2'-thiobis-(4-t-octyl phenolate)]-aquonickel (II) chelate described in Example 1 of German Offenlegungsschrift No. 2,042,652 (prepared from 11.8 g of Compound 1 and 6.2 g of nickel chloride). After two hours heating under reflux, the clear solution obtained was concentrated by evaporation at reduced pressure. 12.7 g (95% of the theoretical amount) of pale green crystals which were completely soluble in ethyl acetate were obtained.

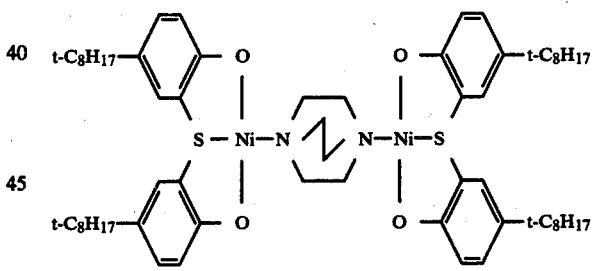

Nickel complex 4

11.8 g of 2,2'-thiobis(4-t-octyl phenol) (=Compound 1) in 80 ml of toluene were added under reflux with stirring to a suspension in 120 ml of toluene of the [2,2'-thiobis(4-t-octyl phenolate)]-aquonickel (II) chelate described in Example 1 of German Offenlegungsschrift No. 2,042,652. All the components were completely dissolved after 3 hours under reflux. The solution was concentrated by evaporation at reduced pressure. The residue was reprecipitated from toluene/petroleum ether. Yield: 22.2 g (90% of theoretical amount) of a pale green powder which was completely soluble in ethyl acetate.

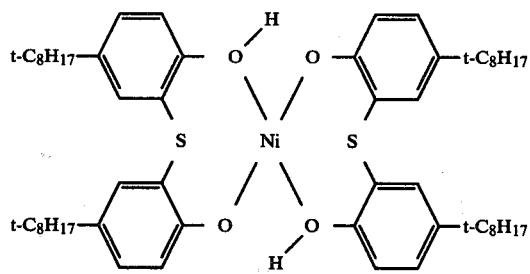

Nickel complex 5

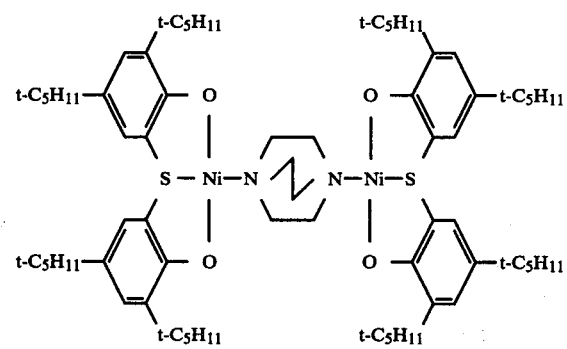

Preparation analogously to nickel complex 3 from Compound 3, nickel chloride and diazabicyclo[2,2,2]octane; light green crystals forming a clear solution in ethyl acetate.

Nickel complex 6

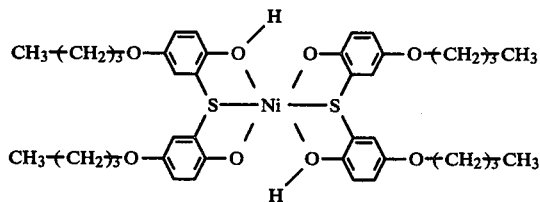

Preparation analogously to nickel complex 4 from Compound 6. Yellowish-green crystal powder forming a clear solution in dichloromethane.

Nickel complex 7

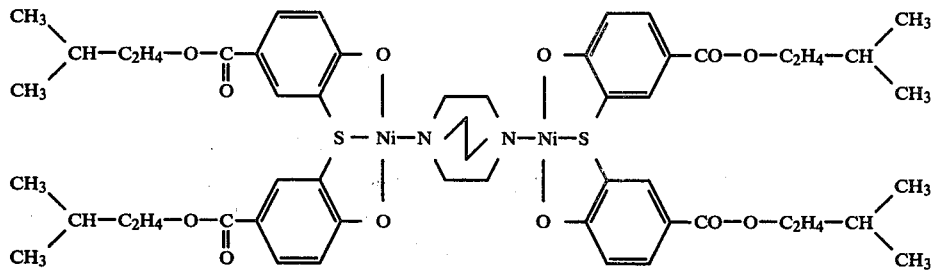

Preparation analogously to nickel complex 3 from Compound II, nickel chloride and diazabicyclo[2,2,-2]octane; green powder soluble in ethyl acetate.

The use of hydrophobic nickel complexes of 2,2'-thio-bisphenols to stabilize polyolefins or rubber and improve their dye absorption capacity is known (German Offenlegungsschrift Nos. 2,009,112, 2,017,044 and 2,302,230).

However, the incorporation of nickel complexes of 2,2'-thio-bisphenols in photographic layers, e.g. in image receptor layers for use in the dye diffusion transfer process, has not hitherto been known and produces surprising results.

Image receptor layers for use in the dye diffusion transfer process contain cationic, low molecular weight, micella-forming mordants or high molecular weight cationic mordants either as solutions or in latex form to fix the image dyes which are usually anionic.

It is known that when anionic image dyes are fixed on cationic mordants, they suffer a considerable loss in light-fastness. This loss depends to a great extent on the structure of the cationic mordant and the form in which it is incorporated and also depends in a manner which is difficult to foresee on the constitution of the image dye which has thus been fixed by the mordant.

In German Offenlegungsschrift No. 2,740,719 it has been proposed to improve the light-fastness of image dyes fixed on cationic mordants by subsequently metallizing them with transition metal ions.

Although this measure in many cases results in a considerable improvement in the light-fastness, it is not generally successful and in many cases produces unforeseeable disadvantages, such as discoloration of the layer on exposure to light.

It is also found that the velocity of complex formation of the image dye depends to a large extent on the manner in which the metal ions are incorporated in the image receptor layer. They are in many cases bound in complex form to low molecular weight or high molecular weight, so-called metal donors which are incorporated in the image receptor layer (e.g. German Offenlegungsschrift No. 3,002,287) and the velocity of complex formation of the image dye decreases drastically with increasing stability of the metal donor complex in the image receptor layer so that the color change to the final image color which accompanies complex formation of the image dye is not completed within the time envisaged for formation of the image.

The cause of the improvement achieved with the invention is not known in detail. The fact that the observable improvements in light-fastness are also achieved with image dyes which have not been metallised is most likely due to a single-oxygen-absorbing effect of the metallizing agents according to the invention or of the bisphenols obtained from them after release of the metal ion. It may also be assumed that the nickel complexes have a general triplet-action.

The following literature is relevant in this connection: J. Griffiths, C. Hawkins, J. Chem Soc. Perkin Trans. II 1977, page 747-752; J. Chem Soc. Chem.

Commun. 1972, p. 463—463; H. Kautsky, H. de Bruin, Natur-Wiss. 19 (1931) 1043, H. Kautsky et al., Ber. dt. chem. Ges. 66, 1588 (1933); P. B. Merkel, W. F. Smith, J. Phys. Chem 84, 2834–40 (1979).

The use of nickel chelates to stabilize photographic color images has often been described. German Offenlegungsschrift No. 2,853,826, for example, describes the use of nickel chelates of thioamides of the picolinic acid or quinaldic acid series of stablize dyes against light. The considerable self color of the nickel chelates described there, however, would cause prohibitive discoloration of the image whites even when present in proportions of only 5 mmol/m² of the image receptor layer.

Only those nickel complexes which do not discolor the image receptor layer beyound densities of 0.07 measured behind blue, green or red filters when present in proportions of 50 mmol/m² are suitable for use in image receptor layers or the dye diffusion transfer process. The nickel chelates of German Offenlegungsschrift No. 2,853,826 as well as those described in German Offenlegungsschriften Nos. 2,854,040, 2,928,042, 2,456,075, 2,846,938, 2,846,937 and 2,853,866 fail to fulfil these requirements.

The nickel complexes described may be used in a wide variety of forms for incorporating nickel ions in layers in a diffusion-fast form without losing their reactivity towards complex-forming substances. Thus, the nickel complexes may be mixed with binders such as gelatine, polyvinyl alcohol, cellulose derivatives or polyacrylamides and used in the form of these mixtures for producing transparent layers.

The nickel complexes described are also suitable as metal donors for incorporation in photographic layers which are required to be colored image-wise or uniformly by a reaction of the complex-bound nickel ions with other organic, either colorless or colored, color-providing complex formers. Uniform coloring is used, for example, when an unwanted image resulting from development of an integral recording material is required to be rendered invisible after image-wise exposure; for example, a negative color image retained in the light-sensitive element may be required to be rendered invisible by uniform coloration if a positive color image is to be produced in the image receptor layer. The nickel complexes described are, however, advantageously used in a combination with an image receptor layer which, together with a layer support, constitutes a so-called image receptor element. Such an image receptor element may be an integral part of a multi-layered light-sensitive color photographic recording material, in which case it either remains attached to the originally light-sensitive element after development or is separated from it. Alternatively, the image receptor element may initially be present as a separate, light-insensitive photographic material which is only brought into contact with the light-sensitive recording material in the course of processing of the latter and may subsequently be separated from it.

The layers capable of being dyed in accordance with the present invention are hydrophilic layers containing a water-insoluble, preferably electro-neutral nickel complex of a bisphenol corresponding to one of the formulae I and II in the form of a finely divided dispersion optionally containing an oil former. These dye absorbent layers may also contain mordants for diffusible anionic dyes or may be in direct contact with suitable mordant layers.

The mordants used for the anionic image dyes may, in principle, be any known cationic, low molecular weight or high molecular weight mordants, e.g. quaternary ammonium or phosphonium salts containing at least one long-chained alkyl or aralkyl group, water-soluble quaternized polyurethanes or polyureas or cross-linked latices containing quaternary salt groups. Suitable examples include the polyurethanes containing cationic glycidyl groups mentioned in German Offenlegungsschrift No. 2,631,521.

The combination of a cationic polyurethane of the last mentioned type (German Offenlegungsschrift No. 2,631,521) with a hydrophobic nickel chelate according to the present invention is capable of giving rise to dye absorbent layers which have considerable advantages, especially in their high fastness to light and the clear color tone of the transferred dyes, if the dye absorbent layer is used as an image receptor layer for the production of dye transfer images.

To prepare the dye absorbent layers according to the invention, the hydrophobic nickel chelates are incorporated in a dispersed form in a layer in the presence of a hydrophilic binder, preferably gelatine. The dispersions are prepared in known manner for this purpose and preferably contain a neutral oil former, e.g. N,N-diethyl-lauric acid amide, tricresyl phosphate, dibutyl phthalate or esters of polyhydric alcohols with long-chained fatty acids.

The oil former content may amount to 10–200% by weight, based on the nickel chelate.

The image receptor elements may be hardened in the usual manner to improve their scratch resistance and limit their liquid absorption when processed with an alkaline medium.

The stability of the nickel chelates which are incorporated in a dispersed form is sufficient to ensure that, during prolonged storage, free nickel ions cannot migrate into the hydrophilic binder phase where they could otherwise diffuse to the incorporated dye-releaser compound and thus cause loss of diffusibility and photographic sensitivity.

The hydrophobic nickel chelates are therefore particularly suitable for the preparation of integral monosheet materials or single sheet materials in which the image receptor element is present in a closed layer unit with the layers of the light-sensitive element from which they may be separated but only by a layer which provides opacity for optical separation.

The photographic material according to the invention having a dye absorbent layer containing the nickel complexes described is suitable for use as an image receptor material for any type of photographic dye diffusion transfer process in which diffusible image dyes or diffusible color formers (image dye precursors) containing substituents capable of chelate formation are used, to be released image-wise and transferred to an image receptor layer. When transfer has been completed, such a photographic material is found to have an image-wise distribution of one or more such dyes in the image receptor layer.

According to one advantageous embodiment of the invention, the photographic material may, in addition to the image receptor element containing the hydrophobic nickel complexes described, also include a light-sensitive element in the form of a sheet comprising at least one layer containing a preferably acid dye or a corresponding precursor compound and at least one light-sensitive layer, in particular a light-sensitive silver halide emulsion layer. The above mentioned dyes and dye precursor compounds will hereinafter be described simply as color providing compounds. The photographic material containing the image receptor layer with the nickel complexes according to the invention may also contain several light-sensitive silver halide emulsion layers with differing spectral sensitivities as well as other layers which are not light-sensitive, such as intermediate layers, covering layers and others fulfilling various functions of the type conventionally used in multi-layered color photographic recording materials.

Photographic materials containing an image receptor layer with nickel complexes according to the invention, i.e. image receptor materials, and in particular color photographic recording materials containing such an image receptor material as an integral constituent thereof, may in addition contain acid layers and so-called retarding layers which together form a so-called combined neutralization system. Such a neutralization system may be arranged in known manner between the layer support and the image receptor layer on that support or it may be arranged in some other position in the combination of layers, e.g. above the light-sensitive layers, i.e. on the far side of these light sensitive-layers when viewed from the image receptor layer. The neutralization system is normally orientated in such a manner that the retarding layer is situated between the acid layer and the position where the alkaline developer liquid or paste comes into operation. Such acid layers, retarding layers or neutralization layers comprising both have been disclosed, for example, in U.S. Pat. Nos. 2,584,030, 2,983,606, 3,362,819 and 3,362,821 and in German Offenlegungsschriften Nos. 2,455,762, 2,601,653, 2,652,464 2,716,505 and 2,816,878. Such a neutralization system may also contain two or more retarding layers in known manner.

According to a particular embodiment, the photographic material may contain one or more pigmented opaque layers permeable to aqueous liquids. These layers may fulfil two functions: they may prevent unwanted access of light to light-sensitive layers and, if they contain a light-colored or white pigment, e.g. $TiO_2$, they may form an aesthetically pleasing background for the colour image produced. Integral color photographic recording materials having such a pigment layer are known, e.g. from U.S. Pat. No. 2,543,181 and German Auslegeschrift No. 1,924,430.

Instead of providing a previously formed opaque layer, means for producing such a layer in the course of the development process may be provided. In accordance with their two functions mentioned above, such pigment layers may be built up of two or more partial layers, one of which, for example, may contain a white pigment while the other may contain a dark, light-absorbent pigment, e.g. carbon black, In a particularly preferred embodiment of the invention, the photographic material is an integral color photographic recording material for carrying out the dye diffusion transfer process and comprises, for example, the following layer elements:

(1) a transparent layer support;
(2) an image receptor layer;
(3) a light-impermeable layer (pigment layer);
(4) a light-sensitive element having at least one light-sensitive silver halide emulsion layer and at least one color-providing compound associated therewith;
(5) a retarding layer;
(6) an acid polymer layer; and
(7) a transparent layer support.

This material may be prepared as two separate parts, namely the light-sensitive part (layer elements 1 to 4) and the cover sheet (layer elements 5 to 7), which are subsequently placed together with their active sides in contact and joined together, optionally using spacer strips to leave space between the two parts for receiving an accurately calculated quantity of developer liquid. The layer elements 5 and 6, which together form the neutralization system, may also be arranged between the layer support and the image receptor layer of the light-sensitive parts, but in the reverse sequence.

Means for introducing a developer liquid between two adjacent layers of the integral recording material may be provided, e.g. in the form of a laterally placed container which can be split open by the action of mechanical forces to release its contents between two adjacent layers of the recording material, in the present case between the light sensitive part and the cover sheet.

In the case of an integral recording material, the light-sensitive element may also form an essential part of the photographic material according to the invention. If the photographic material according to the invention is not itself sensitive to light but consists mainly of layer support and image receptor layer alone, it is brought into contact with the light-sensitive element of a light-sensitive recording material during the development process. In the case of a monochrome dye transfer process, the light-sensitive element contains a light-sensitive silver halide emulsion layer and a color-providing compound associated therewith. This color-providing compound may be situated in a layer adjacent to the silver halide emulsion layer or in the silver halide emulsion layer itself. In the latter case, the color of the image dye is preferably chosen so that the predominant absorption region of the color-providing compound does not coincide with the predominant sensitivity region of the silver halide emulsion layer. For producing true to life colors in multi-colored transfer images, the light-sensitive element contains three such associations of color-providing compound with light-sensitive silver halide emulsion layer, and the absorption range of the image dye obtained from the color-providing compound generally coincides substantially with the region of spectral sensitivity of the associated silver halide emulsion layer. For obtaining the highest possible sensitivity however, it it then advisable to arrange the color providing compound in a separate layer of binder situated behind the silver halide emulsion layer (viewed in the direction of the incident light used for exposure) or to ensure that the color-providing compound has an absorption range different from that of the image dye ("shifted image dyes", U.S. Pat. No. 3,854,945). A shift in the absorption is generally produced in the image receptor layer by complex formation with the nickel ions contain therein if dyes containing substituents capable of chelate formation are used. Color-providing compounds containing such dye residues have been described, for example, in U.S. Pat. No. 3,081,167 and in German Offenlegungsschrift No. 2,740,719.

The color-providing compounds may be colored compounds which are capable of diffusion and begin to diffuse when the layers are treated with an alkaline processing liquid and are fixed by development only in the exposed areas. Alternatively, the color-providing compoundsmay be resistant to diffusion but release a diffusible dye in the course of development.

Color-providing compounds which are a priori diffusible have been disclosed, for example, in German Pat. Nos. 1,036,640, 1,111,936 and 1,196,075. The so-called dye developers described in these Patents contain, in one and the same molecule, a dye residue and a group which is capable of developing exposed silver halide.

Among the known process for the production of color photographic images by the dye diffusion transfer process, increasing importance is being attached to those which are based on the use of color-providing compounds incorporated in a diffusion-fast form from which diffusible dyes or dye precursor compounds are split off image-wise in the course of development and transferred to an image receptor layer. Such non-diffusing color-providing compounds (dye releasers) have been described, for example, in the following documents: U.S. Pat. Nos. 3,227,550, 3,443,939 and 3,443,940. German Offenlegungsschriften No. 1,930,215, 2,242,762, 2,402,900, 2,404,664, 2,505,248, 2,543,902, 2,613,005, 2,645,656, 2,809,716, and Belgian Pat. No. 861,241.

The dye-releasers described in the above-mentioned documents include both those which produce negative color images when conventional negative silver halide emulsions are used and those which produce positive color images with negative silver halide emulsions. If positive color images are to be produced in the former case, it is necessary either to use direct positive silver halide emulsions or, if negative emulsions are used, to employ one of the known reversal techniques e.g. on the basis of the silver salt diffusion process (U.S. Pat. No. 2,763,800) or to effect reversal by using compounds which release development inhibitors as a result of development.

When using image receptor layers in the form of image receptor elements according to the invention, it is preferred to use dye-releasers in which the dye residue contains substituents capable of complex formation. Particular examples include the azo dyes which carry chelate-forming substituents such as OH, —NHR or ring nitrogen atoms adjacent to the azo bond. Color-providing compounds containing such dye residues have been described, for example, in Research Disclosure Publications No. 17334 (September 1978) and No. 18022 (April 1979) and in U.S. Pat. No. 3,081,167, German Offenlegungsschriften No. 31 07 540, No. 31 15 648 and No. 31 17 243, but a stabilizing effect if also obtained when using dye releasers which do not give rise to dyes capable of subsequent complex formation.

EXAMPLE 1

An image receptor sheet according to the invention was prepared by applying the following layers in succession to a polyethylene-laminated paper support (quantities per m²):

Layer 1

4 g of gelatine
2 g of nickel complex 1
2.5 g of tricresyl phosphate
0.03 g of saponin

Layer 2

4 g of cationic polyurethane according to Example 3 of German Offenlegungsschrift No. 2,631,521
5 g of gelatine
0.02 g of saponin

Layer 3

0.1 g of gelatine
0.2 g of instant hardener corresponding to the formula

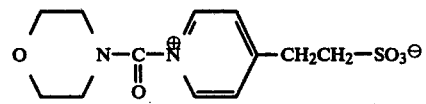

EXAMPLE 2

The procedure was the same as in Example 1 except that a layer 1 which had the following composition was used:

Layer 1

4 g of gelatine
2.8 g of nickel complex 2
2.8 g of tricresyl phosphate and
0.03 g of saponin.

EXAMPLE 3

The procedure was the same as in Example 1 except that layer 1 had the following composition:

Layer 1

4 g of gelatine
2.8 g of nickel complex 3
2.5 g of tricresyl phosphate and
0.03 g of saponin.

EXAMPLE 4

The procedure was the same as in Example 1 except that layer 1 had the following composition:

Layer 1

4 g of gelatine
4.0 g of nickel complex 4
3.0 g of tricresyl phosphate and
0.03 g of saponin.

EXAMPLE 5

The procedure was the same as in Example 1 except that layer 1 has the following composition:

Layer 1

4 g of gelatine
3.2 g of nickel complex 6
3.2 g of tricresyl phosphate and
0.03 g of saponin.

Example 6

The following layers were applied in succession to a polyethylene-laminated paper support (quantites per m²):

Layer 1

5.5 g of gelatine
3.0 g of cationic polyurethane according to Example 3 of German Offenlegungsschrift No. 2,631,521
2.0 g of nickel complex 1
2.5 g of tricresyl phosphate
0.03 g of saponin Layer 2

0.1 g of gelatine 0.2 g of instant hardener corresponding to the formula

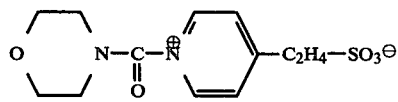

EXAMPLE 7

An image receptor sheet was prepared according to the known art by proceeding as in Example 6 but using a layer 1 which had the following composition:

Layer 1

5.5 g of gelatine 3.0 g of cationic polyurethane according to Example 3 of German Offenlegungsschrift No. 2,631,521 and 0.3 g of saponin.

WORKING EXAMPLE 1

0.03 molor solutions were prepared from the following dyes which are capable of complex formation, and the solutions were made alkaline with 1% NaOH:

Dye A

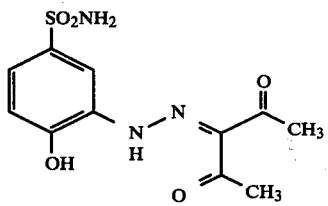

Dye B

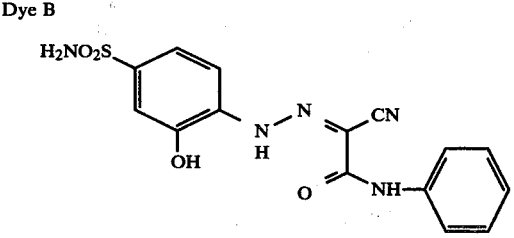

Dye C

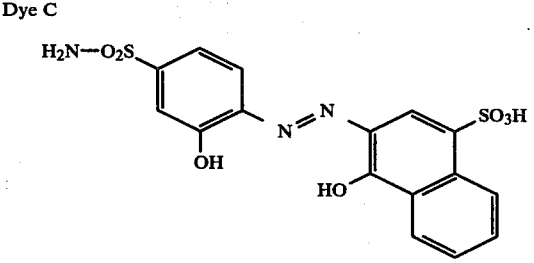

Dye D

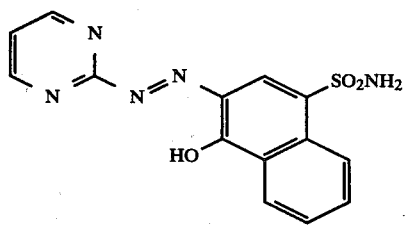

Dye E

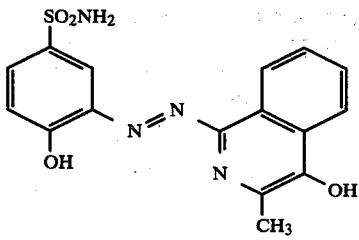

Dye F (Dye of German Offenlegungsschrift No. 31 07 540)

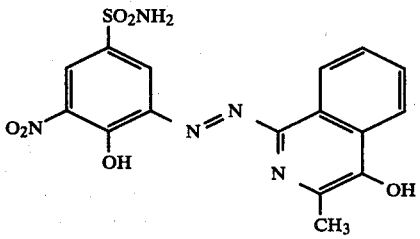

Dye G (Dye 13 of German Offenlegungsschrift No. 31 15 648)

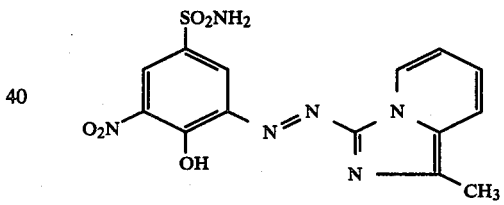

One strip of each of the image receptor sheets 1-6 was dipped into each of these solutions until a density of 1.5 measured behind a filter of the complementary color was obtained. In the case of image receptor sheet 7, the strips were immersed until after-treatment for 30 seconds with a 2% nickel acetate solution resulted in a density of 1.5.

The strips were then after-treated for 1 minute with a 2% sodium succinate solution adjusted to pH 6, and dried.

The results show that the desired color tones are obtained substantially without delay compared with the state of the art and that the exact shades in all cases correspond to those obtained with image receptor sheet 7 after-treated with nickel-acetate. No brown discoloration occurs. Complex formation is instantaneous and a gradual color change is not observed.

To test for light fastness, one strip of each of the image receptor sheets 1, 2 and 7 to which dyes A to G had been transferred was subjected to high intensity exposure to light for 48 hours in a Xeno test apparatus. The percentage losses in density determined after $4.8 \times 10^6$ lux-hours exposure, based on the initial density of 1.5, are summarized in Table 1 below:

TABLE 1

| Image receptor sheet | Density loss (%) | | | | | | |
|---|---|---|---|---|---|---|---|
| | A | B | C | D | E | F | G |
| 1 | 20 | 10 | 5 | 10 | 28 | 30 | 20 |
| 2 | 48 | 11 | 4 | 10 | 38 | 30 | 35 |
| 7 | 50 | 22 | 7 | 25 | 40 | 45 | 30 |

The results enable one to conclude that the light fastness of dye transfers obtained from anionic image dyes capable fo subsequent complex formation can be improved by metallization with hydrophobic nickel chelates according to the invention.

WORKING EXAMPLE 2

The procedure was the same as in Working Example 1 using the following image dyes which are not capable of subsequent complex formation:

Dye H

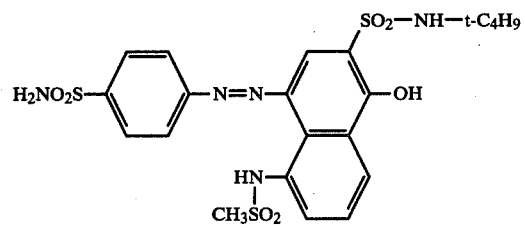

Dye I

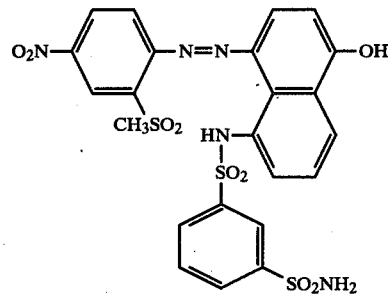

Dye K

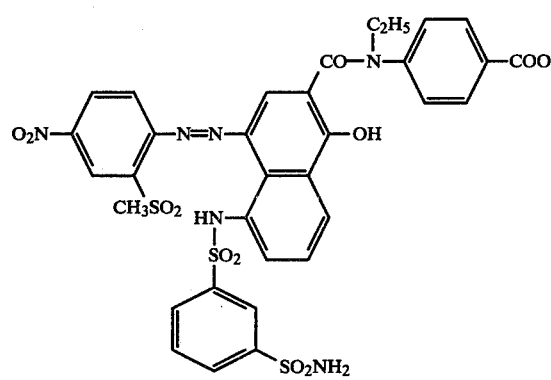

To test for light-fastness, one strip of each of the image receptor sheets 2, 3 and 7 carrying transferred dyes H to K was subjected to high intensity exposure to light for 24 hours in the Xeno test apparatus. The percentage losses in density determined after exposure to $2.4 \times 10^6$ lux-hours, based on the initial density 1.5, are summarized in Table 2 below:

TABLE 2

| Image receptor sheet | Density loss (%) | | |
|---|---|---|---|
| | H | I | K |
| 2 | −21 | −57 | −23 |
| 3 | −21 | −49 | −21 |
| 7 | −40 | −71 | −35 |

The results indicate that the light fastness of colors obtained by the transfer of anionic image dyes which are not capable of complex formation can be improved with hydrophobic nickel chelates according to the invention.

We claim:

1. A photographic material comprising a layer capable of being dyed by organic dyes and containing a metallizing agent for the formation of organic dye-metal complexes arranged on a layer support, said dyeable layer also containing a mordant for diffusible anionic dyes or being in direct contact with a mordant layer containing a mordant for diffusible anionic dyes, wherein said dyeable layer contains dispersed in a hydrophilic binder, as metallizing agent, a water-insoluble nickel complex formed from a 2,2'-bisphenol corresponding to one of the following general formulae I and II:

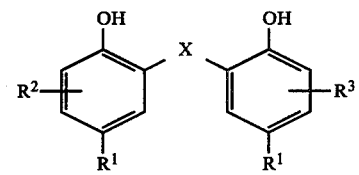

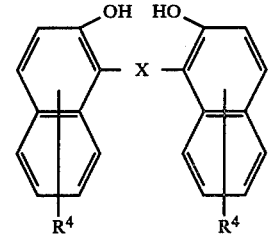

wherein
X denotes —S—,

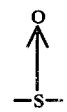

or —SO$_2$—;

R$^1$ denotes a hydrocarbon group having up to 18 C—atoms attached either directly or through —O—, or it denotes a halogen or a group R$^4$;

R$^2$ denotes hydrogen, halogen, alkyl or alkoxy with up to 18 C-atoms, alkenyl, a residue for completing a condensed benzene ring; or a group R$^4$ if R$^1$ does not denote a group R$^4$;

R$^3$ denotes a residue as defined for R$^2$ or a group corresponding to the formula contact with a mordant layer containing a mordant for diffusible anionic dyes wherein said dyeable layer contains dispersed in a hydrophilic binder, as metallizing agent, a water-insoluble nickel complex formed from a 2,2'-bisphenol corresponding to one of the following general formula I and II:

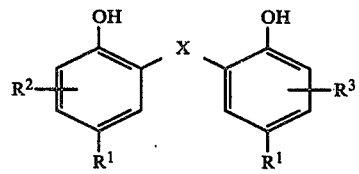

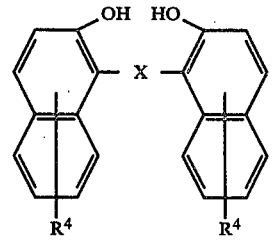

wherein
X denotes

or —SO$_2$—;
R$^1$ denotes a hydrocarbon group having up to 18 C-atoms attached either directly or through —O—, or it denotes a halogen or a group R$^4$;
R$^2$ denotes hydrogen, halogen, alkyl or alkoxy with up to 18 C-atoms, alkenyl, a residue for completing a condensed benzene ring; or a group R$^4$ if R$^1$ does not denote a group R$^4$;
R$^3$ denotes a residue as defined for R$^2$ or a group corresponding to the formula:

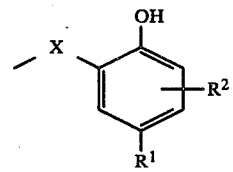

wherein X, R$^1$ and R$^2$ have the meaning indicated above;
R$^4$ denotes —CO—O—R$^5$,

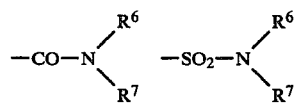

—NH—CO—R$^8$ or —HN—SO$_2$R$^9$;
R$^5$ denotes alkyl, aralkyl or cycloalkyl having up to 8 C-atoms;
R$^6$ and R$^7$ denote hydrogen, alkyl, aralkyl, aryl or cycloalkyl or together a denote a residue for completing a 5-, 6- or 7-membered cyclic amino group;

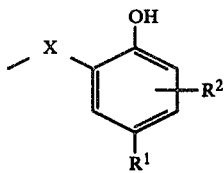

wherein X, R$^1$ and R$^2$ have the meaning indicated above;
R$^4$ denotes —CO—O—R$^5$,

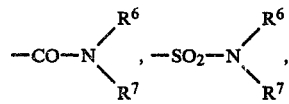

—NH—CO—R$^8$ or —NH—SO$_2$R$^9$;
R$^5$ denotes alkyl, aralkyl or cycloalkyl having up to 8 C-atoms;
R$^6$ and R$^7$ denote hydrogen, alkyl, aralkyl, aryl or cycloalkyl or together denote a residue for completing a 5-, 6- or 7-membered cyclic amino group;
R$^8$ denotes alkyl, aralkyl, aryl, OR$^5$ or

and
R$^9$ denotes alkyl, aryl or

2. A photographic material as claimed in claim 1, wherein the dyeable layer contains a nickel complex of a 2,2'-bisphenol of formula I wherein R$^1$ denotes alkyl and R$^2$ and R$^3$ denote hydrogen, chlorine or alkyl.

3. A photographic material as claimed in claim 1, wherein the dyeable layer contains a nickel complex of a 2,2'-bisphenol of formula II wherein R$^4$ denotes a group corresponding to the formula

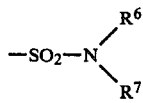

in the 6-position (of the naphthalene ring), wherein R$^6$ denotes alkyl and R$^7$ denotes hydrogen or alkyl.

4. A photographic material as claimed in claim 1 wherein the dyeable layer is an essential part of an image receptor element for the dye diffusion process.

5. A multi-layered light-sensitive color photographic material comprising a light-sensitive element which contains at least one silver halide emulsion layer and a color providing compound and also comprising as an integral constituent of the color photographic material an image receptor element which contains as an essential part a layer capable of being dyed by organic dyes and containing a metallizing agent for the formation of organic dye-metal complexes which dyeable layer contains a mordant for diffusible anionic dyes or is in direct $R^8$ denotes alkyl, aralkyl, aryl, $OR^5$ or
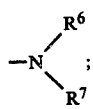
and
$R^9$ denote alkyl, aryl or
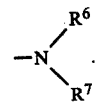
* * * * *